United States Patent [19]

Sekiguchi

[11] Patent Number: 4,914,512
[45] Date of Patent: Apr. 3, 1990

[54] ELECTRONIC ENDOSCOPE APPARATUS CAPABLE OF DISPLAYING HEMOGLOBIN CONCENTRATION ON COLOR IMAGE

[75] Inventor: Tadashi Sekiguchi, Saitama, Japan

[73] Assignee: Kabushiki Kaisha Toshiba, Kawasaki, Japan

[21] Appl. No.: 298,624

[22] Filed: Jan. 18, 1989

[30] Foreign Application Priority Data

Jan. 19, 1988 [JP] Japan .................................. 63-7515
Mar. 3, 1988 [JP] Japan .................................. 63-48587

[51] Int. Cl.$^4$ .......................... A61B 1/06; H04N 7/18
[52] U.S. Cl. ......................................... 358/98; 128/6
[58] Field of Search ................ 358/98, 211, 27, 28, 358/29; 128/4, 6

[56] References Cited

U.S. PATENT DOCUMENTS

| | | | |
|---|---|---|---|
| 4,593,313 | 6/1986 | Nagasaki et al. ..................... | 358/98 |
| 4,716,457 | 12/1987 | Matsuo ................................... | 358/98 |
| 4,737,842 | 4/1988 | Nagasaki ............................... | 358/98 X |
| 4,768,089 | 8/1988 | Kato ....................................... | 358/98 |

OTHER PUBLICATIONS

E. Gordy, et al., "Journal of Biological Chemistry", *Spectrophotometric Studies*, vol. 227 (1957) pp. 285–299.

*Primary Examiner*—Howard W. Britton
*Assistant Examiner*—Victor R. Kostak
*Attorney, Agent, or Firm*—Foley & Lardner, Schwartz, Jeffery, Schwaab, Mack, Blumenthal & Evans

[57] ABSTRACT

In an electronic endoscope apparatus, there are provided a brightness converter for converting brightness of a color image signal of a biological body under examination while the biological body is irradiated by monochromatic light; a plurality of image memories for storing a plurality of brightness-converted image signals; and a calculating circuit for calculating the plurality of brightness-converted image signals to obtain a concentration of hemoglobin of the biological body and an oxygen saturation of hemiglobin thereof. Then, the concentration of hemoglobin and oxygen saturation of the biological body are displayed as a color image.

24 Claims, 9 Drawing Sheets

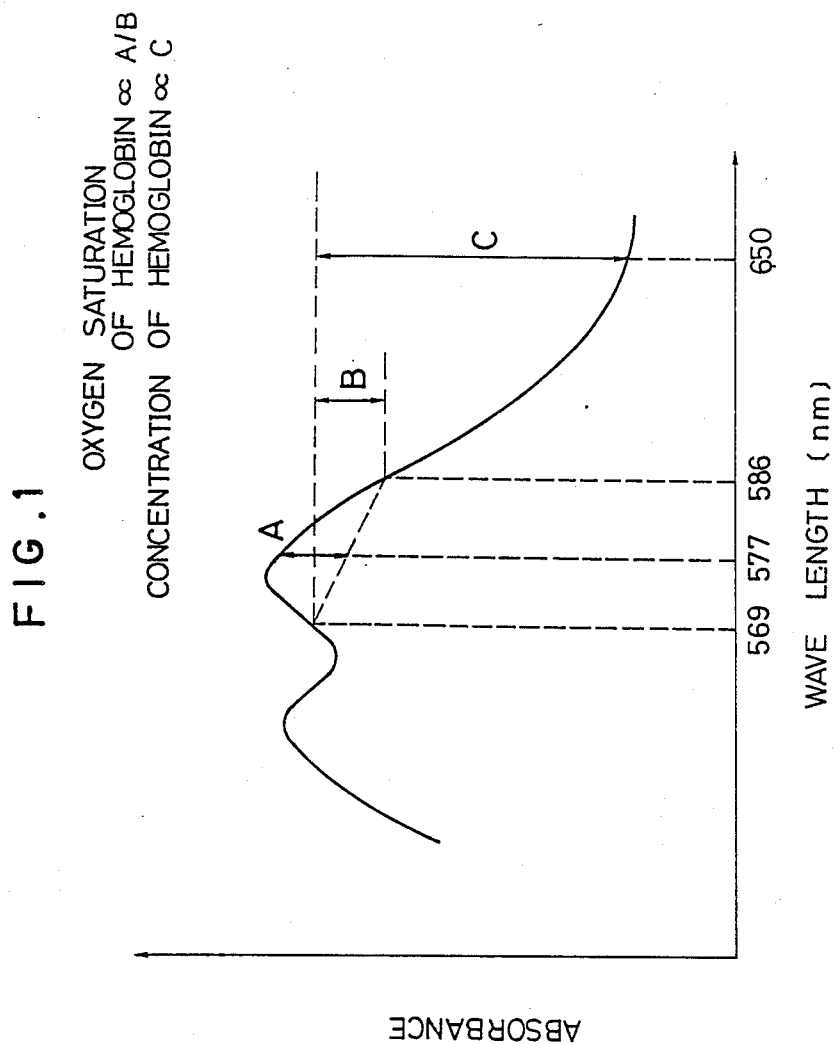

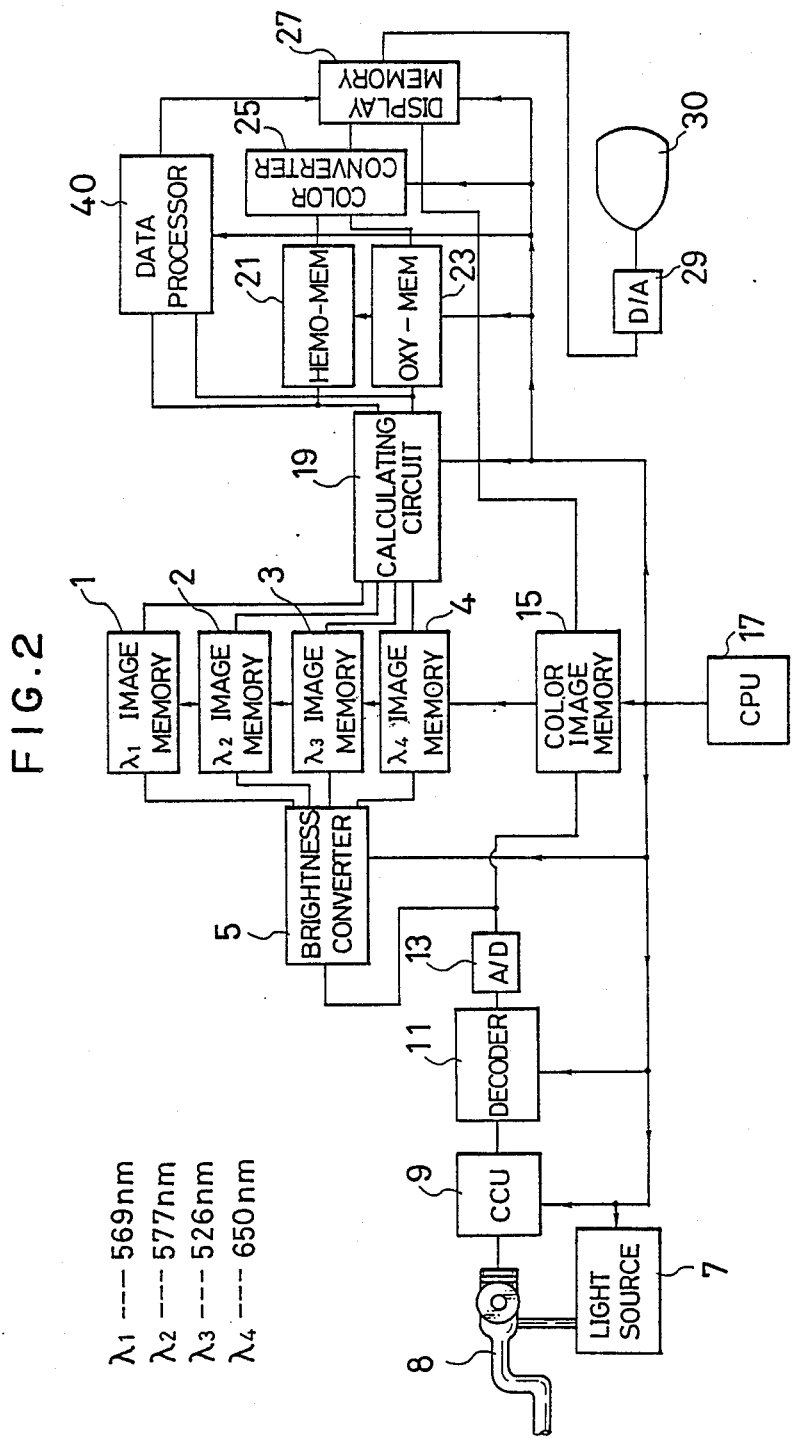

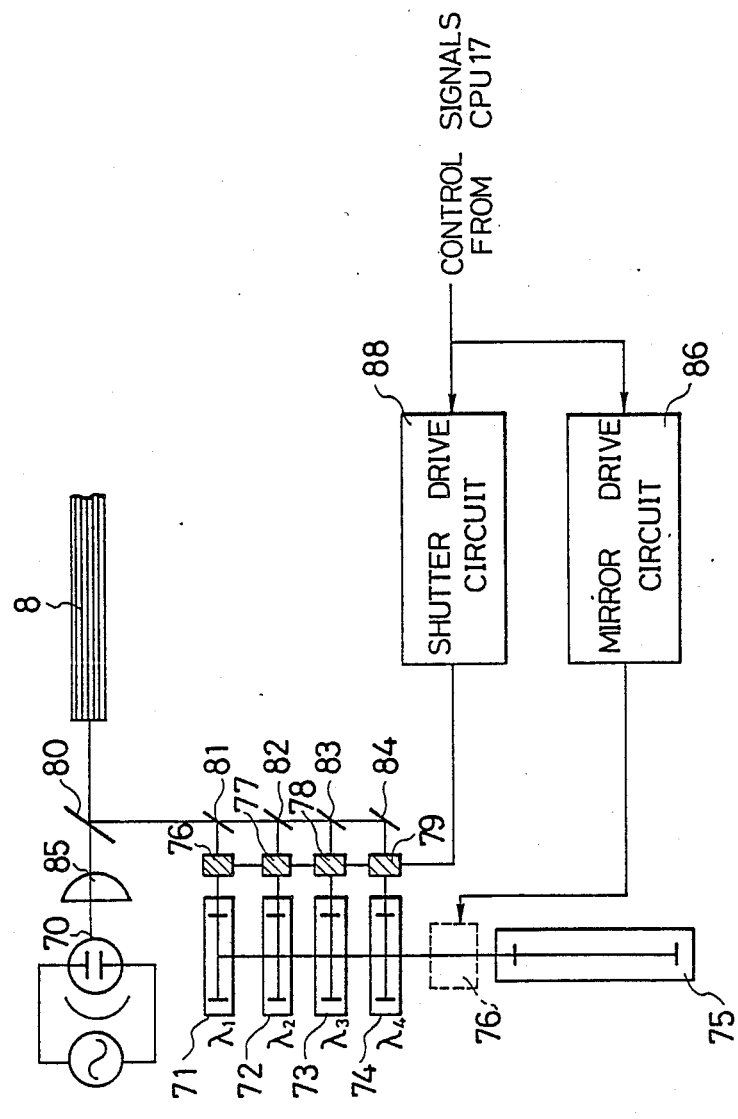

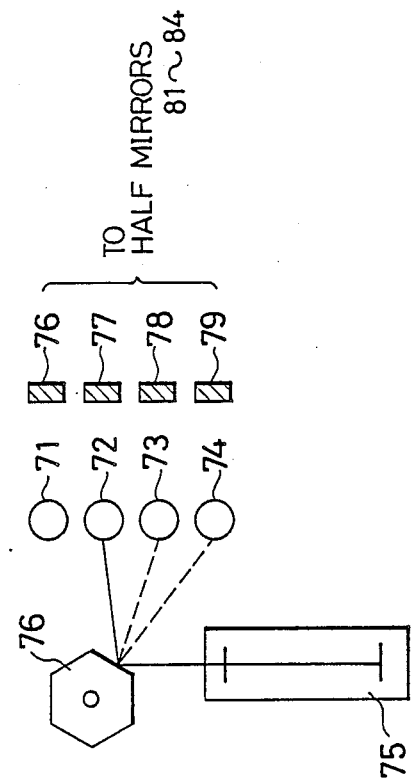

ELECTRONIC ENDOSCOPE APPARATUS CAPABLE OF DISPLAYING HEMOGLOBIN CONCENTRATION ON COLOR IMAGE

BACKGROUND OF THE INVENTION

1. Field of the Invention

The present invention generally relates to an electronic endoscope apparatus for acquiring medical information within a biological body by employing a solid-state imaging element or a camera tube. More specifically, the present invention is directed to an electronic endoscope apparatus capable of displaying as an image or numerical data, functional information and shapes of, for instance, a mucous membrane of a stomach, e.g., a concentration of hemoglobin and oxygen saturation of hemoglobin.

2. Description of the Related Art

In a conventional electronic endoscope apparatus, the functional information of a biological body, such as mucous membrane of a stomach, may be observed by firstly photographing the biological body with a plurality of monochromatic lights having different wavelengths so as to acquire a plurality of images thereof. Then, differences between a plurality of absorbances with respect to the monochromatic light having the different wavelengths are calculated from the acquired image information.

In the absorption spectrum curve of, for instance, the concentration of hemoglobin under the mucous membrane as illustrated in FIG. 1, it is known from, e.g., Journal of Biological chemistry, vol. 227 issued in 1957, page 285, that the concentration of hemoglobin is directly proportional to a difference of the absorbance denoted by "C", which is plotted at two different wavelengths of 569 nm (nano meters) and 650 nm. Similarly as is known in this field, the oxygen saturation of hemoglobin is directly proportional to an amount calculated from a ratio of A to B (A/B). As a result, the differences in the absorbances measured at four wavelengths of 569, 577, 586 and 650 nm are calculated and then processed, so that the concentration of the hemoglobin under the mucous membrane, or oxygen saturation of hemoglobin, may be displayed as an image.

As previously described in the conventional electronic endoscope apparatus, functional information can be observed by irradiating the monochromatic light having four different wavelengths to the mucous membrane in order to acquire four sets of the monochromatic light images, by performing a predetermined calculation for these monochromatic light images so as to obtain the concentration of hemoglobin under the mucous membrane and also the oxygen saturation of hemoglobin as the functional information, and by displaying the resultant data as the images. Accordingly, the above-described functional information can be imaged. To obtain such a functional information of the biological body, the external memories, e.g., magnetic tapes and floppy disks are utilized and the data processing is carried out by the off-line process.

In the conventional electronic endoscope apparatus, on the other hand, the acquired functional information is displayed either as the monochromatic image, or the so-called "quasi-colored image" by allocating the R, G, B signals to the functions of the functional information without introducing the definite color allocation basis.

As a consequence, the conventional electronic endoscope apparatus have the following drawbacks.

First, the functional information of the biological body to be examined is once stored into the external memory devices. Thereafter, the functional information data stored in the external memory devices are read and calculated. Then, the acquired functional information is displayed on the display unit of the conventional electronic endoscope apparatus. As a result, such a functional information cannot be provided in a real time for the diagnostic purpose.

Since the image data obtained by using the monochromatic light are stored in the memory device having the large memory capacity which is originally used for storing the color image data of the biological body, a large number of the memory device having the large memory capacity is required for storing both the color image data and monochromatic light image data, resulting in the high-cost endoscope apparatus.

Moreover, when the functional information of the biological body to be examined is displayed as the monochromatic (black/white) image, such a black/white image is not visible for an operator in the conventional electronic endoscope apparatus. Also according to a so-called "quasi-colored imaging method" where the R.G.B. signals are arbitrarily allocated to the various functions of the functional information. Namely, there is no definite rule to allocate the R,G,B signals. In addition, there is no linear relationship between changes in the concentration of hemoglobin under the mucous membrane as the functional information and changes in the hue of the displayed image thereof. As a consequence, it is very difficult to correctly grasp the functional information of the mucous membrane under examination from the displayed quasi-colored images in the conventional electronic endoscope apparatus.

SUMMARY OF THE INVENTION

The present invention has been made in an attempt to solve the above-described conventional problems, and has an object to provide an electronic endoscope apparatus capable of acquiring, calculating and image-processing shapes and functional information of a biological body under examination in a real time.

Another object of the present invention is to provide an electronic endoscope apparatus constructed of a simple circuit arrangement in low cost by employing a plurality of memory devices having small memory capacities, instead of employing a plurality of memory devices having large memory capacities for storing color images.

A still further object of the present invention is to provide an electronic endoscope apparatus capable of displaying as the color image the functional information of the biological body under examination, in which each function of the functional information is allocated to one of three color primary elements, i.e., hue, color saturation and brightness and the respective color primary elements are controlled based upon the corresponding functional information.

These objects and other features of the invention are accomplished by providing an electronic endoscope apparatus comprises:

a light source (7) for separately producing colored light having a predetermined light wave band and a plurality of monochromatic lights having a plurality of different wavelengths ($\lambda_1:\lambda_2:\lambda_3:\lambda_4$);

a scope (8) for producing an image signal of a biological body under examination while the biological body is irradiated by one of the color light and monochromatic light;

a color signal processing circuit (9; 11; 13) for processing the image signal derived from scope (8) so as to obtain a color television signal;

a circuit (5) for converting brightness of the color television signal acquired while the biological body is irradiated by one of the monochromatic light to obtain a brightness-converted image signal; and, a calculating circuit (19) for calculating a plurality of brightness-converted image signals to obtain a functional-information signal representative of functional information on the biological body;

BRIEF DESCRIPTION OF THE DRAWINGS

For a better understanding of the present invention, reference is made to the following descriptions in conjunction with the accompanying drawings, in which:

FIG. 1 is a graphic representation to explain a relationship between wave length and light absorbance of human hemoglobin;

FIG. 2 is a schematic block diagram of an electronic endoscope apparatus according to a first preferred embodiment of the invention;

FIG. 3A schematically illustrates an arrangement of the light source 7 employed in the endoscope apparatus shown in FIG. 2;

FIG 3B illustrates the reflection of laser lights using a rotating mirror;

DETAILED DESCRIPTION OF THE PREFERRED EMBODIMENTS

Figure 4:
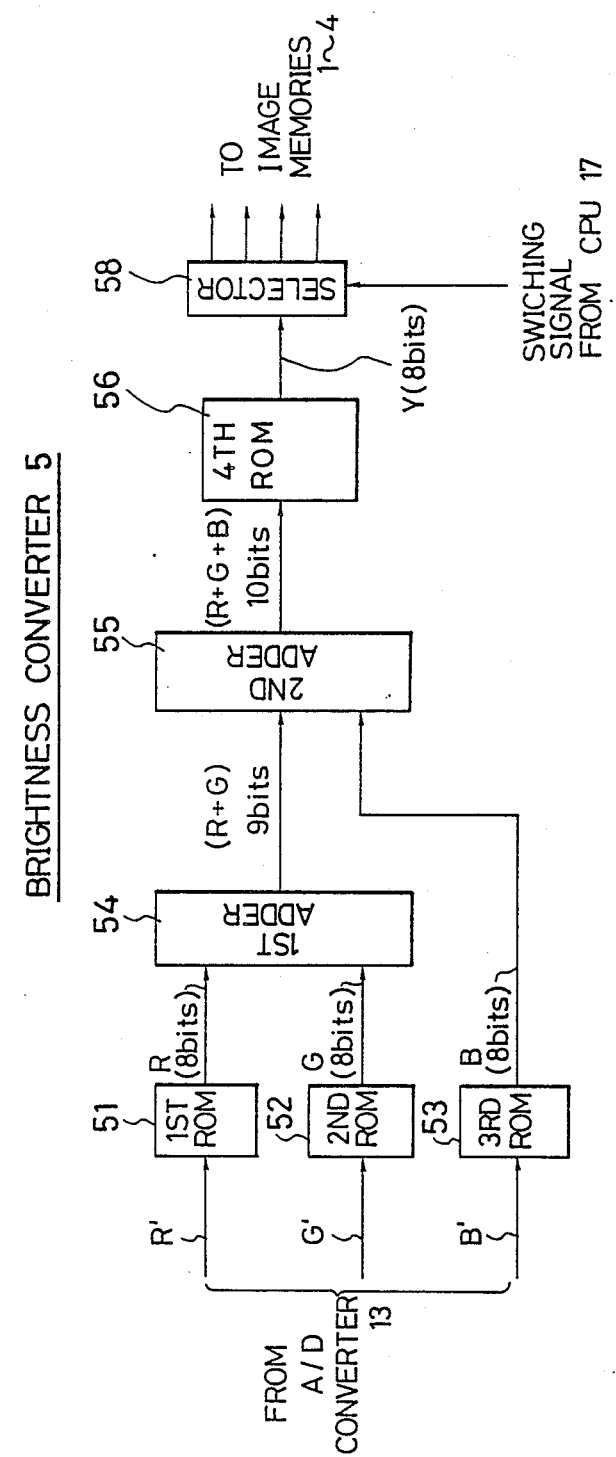
FIG. 4 is a block diagram of an internal circuit of the brightness converter 5 employed in the endoscope apparatus shown in FIG. 2.

Arrangement of First Endoscope Including Brightness Conversion Circuit

FIG. 2 is a schematic block diagram of a complementary color filter type electronic endoscope apparatus, according to a first preferred embodiment of the invention, capable of displaying a concentration of hemoglobin and oxygen saturation of hemoglobin under a mucous membrane as the functional information of a biological body under examination, and also of displaying a color image of tissue thereof.

The electronic endoscope apparatus shown in FIG. 2 includes four image memory devices 1 through 4, a brightness converter 5, a light source 7, a fiber scope 8, a camera control unit (referred to as a "CCU") 9, a decoder 11, an analog-to-digital (A/D) converter 13, a color image memory device 15, a central processing unit (CPU) 17, and a calculating circuit 19. The electronic endoscope apparatus further includes an image memory 21 for storing the concentration of hemoglobin under the mucous membrane (simply referred to as a "hemoglobin data memory"), another image memory 23 for storing the oxygen saturation of hemoglobin, a color converter 25, a display memory 27, a digital-to-analog (D/A) converter 29 and a display unit 30.

Although not shown in FIG. 2, a CCD (charge-coupled device) as an image sensor is mounted in the distal end of the scope 8 in the preferred embodiment. However, the present invention is not limited to this type of the scope. For instance, such a CCD may be mounted on a camera operating unit of a fiber scope, or the normal endoscope camera employing the vidicon may be employed instead of this CCD.

In the electronic endoscope apparatus shown in FIG. 2, the memory capacity of each of the image memories 1 to 4 is selected to be 256 Kilobytes (KB), whereas that of the normal color image memory 15 is approximately 3 times higher than the first-mentioned memory capacity, i.e., 640 KB.

OVERALL OPERATION OF FIRST ENDOSCOPE

Referring now to FIG. 2, a signal processing operation of the electronic endoscope apparatus according to the first preferred embodiment will be described so as to display the functional information of the biological body under examination on the display unit 30.

A picture signal is derived from the CCD image sensor having the complementary filters (not shown in detail), which is mounted on the distal end of the fiber scope 8, while irradiated by the selected monochromatic light from the light source 7 via the scope 8. This scope 8 has been inserted into the biological body under examination. The picture signal is converted into the corresponding NTSC color signal in CCU 9. Then, the NTSC color signal is further processed in the decoder 11 so as to produce a color image signal, i.e., R (red), G (green), and B (blue) signals. The resultant R.G.B signals are converted in the A/D converter 13 into the corresponding digital R.G.B data. These digital R.G.B data are transferred to the brightness converter 5 to produce the brightness-converted R.G.B data. The function of this brightness converter 5 is to sum the signal components of three R.G.B data with respect to the respective pixels of the image of the biological body (will be described later).

The brightness-converted R.G.B data, namely B/W image information is acquired by irradiating the monochromatic light having a predetermined wavelength i ("i" being 1, 2, 3 and 4). The resultant B/W image information of the biological body is stored into the corresponding image memory devices 1 to 4. It should be noted that the wavelength, $\lambda_1$ corresponds to 569 nanometers (nm), the wavelength $\lambda_2$ is equal to 577 nm, the wavelength $\lambda_3$ is 586 nm, and the wavelength $\lambda_4$ is selected to be 650 nm.

The B/W image information which has been stored in the respective image memory devices 1 to 4 is transferred to the calculating circuit 19. In accordance with the calculating operation by the calculating circuit 19, two functions of the functional information of the biological body, i.e., the concentration of hemoglobin under the mucous membrane and the oxygen saturation of hemoglobin can be obtained.

CONCENTRATION OF HEMOGLOBIN

To obtain the concentration of hemoglobin under a mucous membrane of, e.g., a stomach of a biological body under examination, as one of the functional information, the B/W image information stored into the fourth image memory device 4, i.e., the absorbance calculated from the brightness of the B/W image data acquired at the wavelength of 650 nm is subtracted from the B/W image information stored in the first image memory device 1, i.e., another absorbance calculated from the brightness of the B/W image data acquired at the wavelength of 569 nm (absorbance$_{569nm}$ − absorbance$_{650nm}$). This subtraction process is carried out for each of the pixels of the B/W image. In other words, the concentration of the hemoglobin is obtained by calculating the symbol "C" shown in the absorption spectrum curve of FIG. 1.

OXYGEN SATURATION OF HEMOGLOBIN

Also, to obtain oxygen saturation of hemoglobin under the stomach's mucous membrane, as another functional information, two amounts denoted by "A" and "B" shown in the absorption spectrum curve are calculated in the calculating circuit 19 from the B/W image information stored in the first to third image memory devices 1 to 3. Thereafter, a ratio of "A" to "B" is calculated for each of the pixels of the B/W image.

Referring back to the signal processing operation of the electronic endoscope apparatus according to the first preferred embodiment, the B/W image information, or data stored in the respective image memory devices 1 to 4 are transferred to the calculating circuit 19 under the following condition. That is, one unit of the data transfer is selected to be the data acquired during one horizontal scanning period of the CCD image sensor, i.e., the brightness data of the B/W image relating to 512 pixels thereof. Then, according to the first preferred embodiment, the data transfer is carried out under the data acquired during one horizontal scanning period of the CCD image sensor as one data transfer unit in the circuits 25, 27 and 29.

In accordance with the above-described data transfer and signal processing method, the memory capacities required for the respective circuits, e.g., the calculating circuit 19 and hemoglobin concentration memory device 21 have a small memory capacity for storing just the data acquired during one horizontal scanning period of the CCD image sensor. This required memory capacity is considerably smaller than that required for transferring all image data at one time.

As previously described, two types of the functional information, i.e., the concentration of hemoglobin in the mucous membrane and the hemoglobin oxygen saturation thereof which have been acquired in the calculating circuit 19 are separately transferred to the memory device 21 for the concentration of hemoglobin, and memory device 23 for the oxygen saturation to be stored therein. It should be noted that the memory capacities of these memory devices 21 and 23 correspond to the amount of the data acquired during 1 horizontal scanning period of the CCD image sensor, i.e., 512 bytes.

The functional information data read out from these memory devices 21 and 23 are supplied to the color converter 25. In the color converter 25, the colors to be displayed on the display device 30 are determined in accordance with the combination of two data values read out from the memory devices 21 and 23 every pixel of the B/W image information.

In the electronic endoscope apparatus according to the first preferred embodiment, the following known color conversion method is introduced. That is to say, the hue corresponds to the concentration of hemoglobin, in which as the concentration of hemoglobin is increased, the hue is changed from the cold color to the warm color, e.g., blue, green and red. The brightness corresponds to the hemoglobin oxygen saturation, in which as the hemoglobin oxygen saturation is increased, the brightness is increased.

The information relating to the colors determined in the color converter 25 every pixel is transferred to the display memory 27, and stored therein. According to the first preferred embodiment, the memory capacity of this display memory 27 similarly corresponds to the data amount acquired during 1 horizontal scanning period of the color image displayed on the display unit 30, i.e., 1.5 K bytes.

The functional information data which have been converted into the colors determined in the color converter 25 every pixel and read out from the display memory 27, are converted into the D/A converter 29 into the corresponding analog functional-information signal. Then, the analog functional-information signal is supplied to the display unit 30 by which the acquired functional information is displayed in the color image.

According to the first preferred embodiment, as previously described, the colors of the respective pixels of the displayed color image correspond to the combination of the above-described two different functional information relating to the pixels in question. As a consequence, this color image represents the above-described two different functional information of the biological body under examination.

CPU 17 including a sync signal generator (not shown in detail) performs the entire controlling operations of the electronic endoscope apparatus, e.g., a driving operation of the light source 7, and a signal processing operation of the calculating circuit 19, as illustrated by arrows in FIG. 2.

Under the control of CPU 17, the signal transfer and processing operation of the first preferred embodiment are carried out in the pipe-line system. That is, while the functional information data acquired during 1 horizontal scanning period of the CCD image sensor are read out from the first to fourth image memory devices 1 to 4 for the display purpose, and thereafter signal-processed in the calculating circuit 19, the functional information data acquired during the subsequent 1 horizontal scanning period are read out from the first to fourth image memory devices 1 to 4 so that the functional information data are continuously processed in the electronic endoscope apparatus shown in FIG. 2.

In the electronic endoscope apparatus shown in FIG. 2, on the other hand, for acquiring the normal color image of the biological body during examination, a xenon lamp of the light source 7 is driven (will be discussed later), the picture data derived from the A/D converter 13 are stored into the color image memory 15, and thereafter transferred via the display memory unit 27, and D/A converter 29 to the display unit 30. Then, the image of the biological body is displayed on the display unit 30 for medical diagnostic purposes.

Also in the electronic endoscope apparatus shown in FIG. 2, a data processor 4 is connected between the output terminals of the calculating circuit 19 and the input terminal of the display memory 27. Under the control of the data processor 40, the numerical data of the functional information are obtained from the calculated functional information data. The numerical data such as the concentration of hemoglobin are temporarily stored in the display memory 27 and then displayed on the display unit 30.

The numerical data may be recorded on an external recorder, if required.

LIGHT SOURCE

FIG. 3 is a schematic block diagram of a detailed arrangement of the light source 7 shown in FIG. 2. FIG. 3A schematically illustrates the entire arrangement of the light source 7 and FIG. 3B schematically illustrates conditions of laser light selections by a mirror polygon.

In FIG. 3A, a xenon lamp 70 used for the normal color image photographying operation and four different chroma lasers 71 to 74 are employed in the light source 7. These dye lasers 71 to 74 correspond to the wavelengths of $\lambda_1$ (569 nm), $\lambda_2$ (577 nm), $\lambda_3$ (586 nm) and $\lambda_4$ (650 nm), respectively. These four dye lasers 71 to 74 are combined with an argon laser 75. Laser light emitted from the argon laser 75 is reflected by the mirror polygon 76, and then the reflected laser light is incident upon the corresponding dye lasers 71 to 74. As a result, the desired monochromatic laser light is supplied via shutters 76 to 79 to half mirrors 81 to 84, respectively. The monochromatic laser light is reflected from the corresponding half mirrors 81 to 84, and thereafter supplied via another half mirror 80 to a light inlet of the scope 8. On the other hand, light emitted from the xenon lamp 70 is focused by a lens 85 and penetrates through the half mirror 80, and finally supplied to the light inlet of the scope 8.

The above-described mirror polygon 76 is driven by a mirror drive circuit 86 in response to the control signal derived from CPU 17. Also, the shutters 76 to 79 are driven by a shutter drive circuit 88 in response to another control signal from CPU 17.

To display the above-described two different functional information of the biological body, four different dye lasers 71 to 74 are successively driven, and four pieces of the monochromatic laser light having four specific wavelengths $\lambda_1$ to $\lambda_4$ are supplied to the light inlet of the fiber scope 8 (see FIG. 3B). In case of the normal photographic operation of the electronic endoscope apparatus shown in FIG. 2, all of the shutters 76 to 79 are closed under the control of the shutter drive circuit 88 so as not to supply the above-described monochromatic laser light to the light inlet of the scope 8, and also the xenon lamp 7 is turned on to supply the xenon lamp light to the light inlet of the scope 8.

BRIGHTNESS CONVERTER

Referring now to FIG. 4, an internal circuit arrangement of the brightness converter 5 employed in the electronic endoscope apparatus according to the first preferred embodiment will be described.

As previously described, the R,G,B signals are derived from the decoder 11 shown in FIG. 2. These signals have been gamma-corrected in order to be matched with the phosphorous materials of the display screen 30, as is well known in the art, which are represented by R', G', B' signals in FIG. 4. These R', G', B' signals are non-linear signals. These non-linear R', G', B' signals are A/D-converted in the A/D converter 13 to produce R', G', B' data. Then, the R', G', B' data are supplied to first to third ROMs 51, 52 and 53, respectively. These data are raised to 2.2 powers so as to obtain linear R, G, B data. The resultant data are supplied to a selector 58. In response to the switching signal derived from CUP 17, input data selecting operations are carried out in this selector 58 in synchronism with the selecting operation of the dye lasers 71 to 74 employed in the light source 7. When, for instance, the dye laser 71 having the wavelength $\lambda_1$ is actuated, the 8-bit Y data inputted into this selector 58 are switched in the selector 58 to be supplied to the first image memory device 1, shown in FIG. 2.

ADVANTAGES OF FIRST ELECTRONIC ENDOSCOPE

While has been described above, the electronic endoscope apparatus according to the first preferred embodiment, shown in FIGS. 2 to 4, has the following advantages.

First, since the image memories having the small memory capacities are employed, which is different from the conventional electronic endoscope apparatus including the external memory devices such as floppy disks, for the same purpose, the acquired functional information data can be processed in a real time.

Instead of employing a memory device having a large memory capacity for storing the normal color images, image memory devices having considerably smaller memory capacities can be utilized for the same purpose, i.e., storage of the functional information data. As a result, the number of the memory boards can be reduced and therefore a low cost endoscope apparatus can be manufactured.

SECOND ENDOSCOPE INCLUDING FUNCTIONAL-INFORMATION COLOR DISPLAYING CIRCUIT

Figure 5:
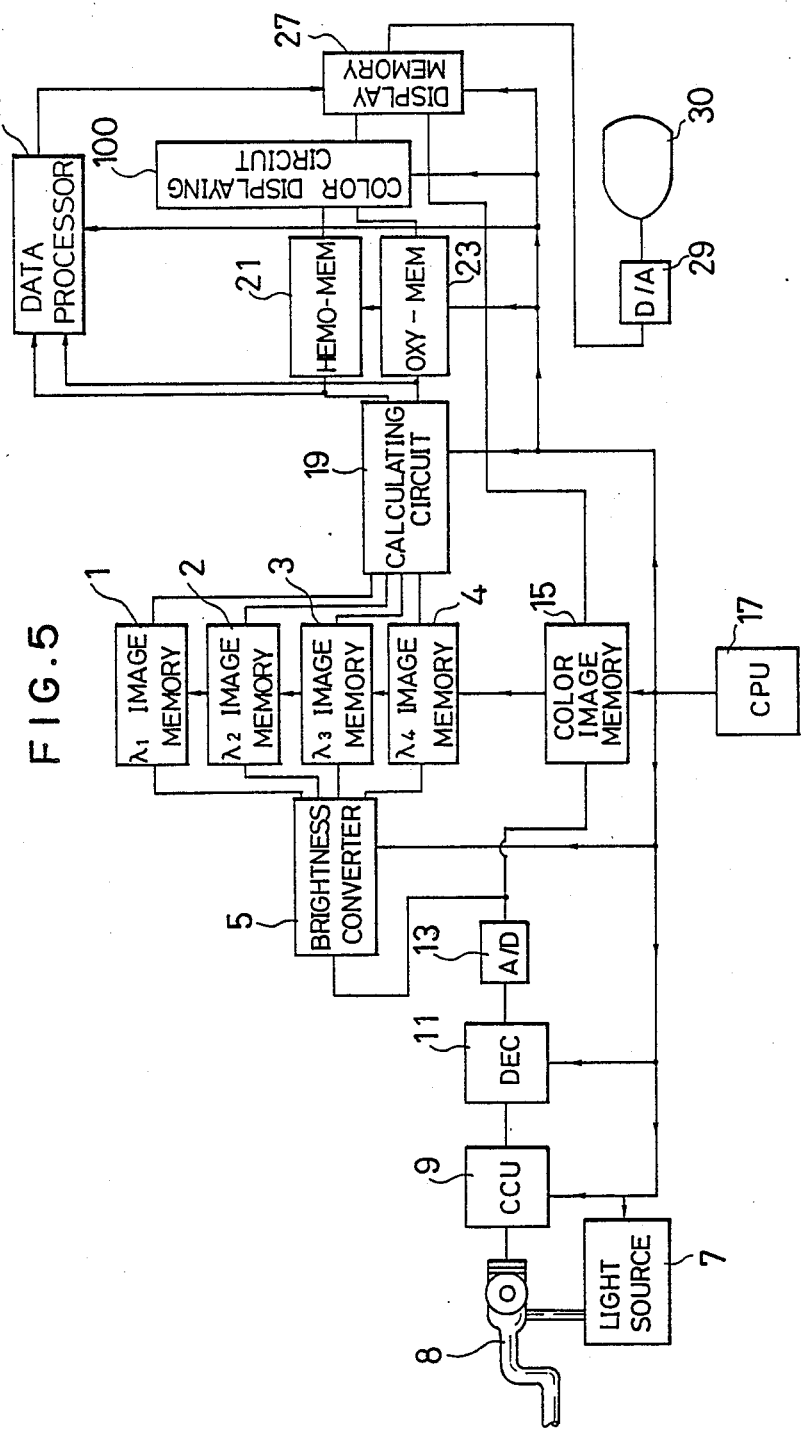
FIG. 5 is a schematic block diagram of an electronic endoscope apparatus according to a second preferred embodiment.

FIG. 5 is a schematic block diagram of an electronic endoscope apparatus including a functional-information color displaying circuit 100 according to a second preferred embodiments of the invention.

As apparent from the circuit diagram shown in FIG. 5, the major circuit of this second endoscope apparatus is similar to that of the previous first endoscope apparatus. The same or similar circuit elements are indicated by the same reference numerals employed in FIG. 2. The operations of these same or similar circuit elements will be omitted.

In FIG. 5, a functional-information color displaying circuit 100 is connected to the output terminals of the hemoglobin-concentration image memory 21 and hemoglobin-oxygen saturation image memory 23.

Figure 6:
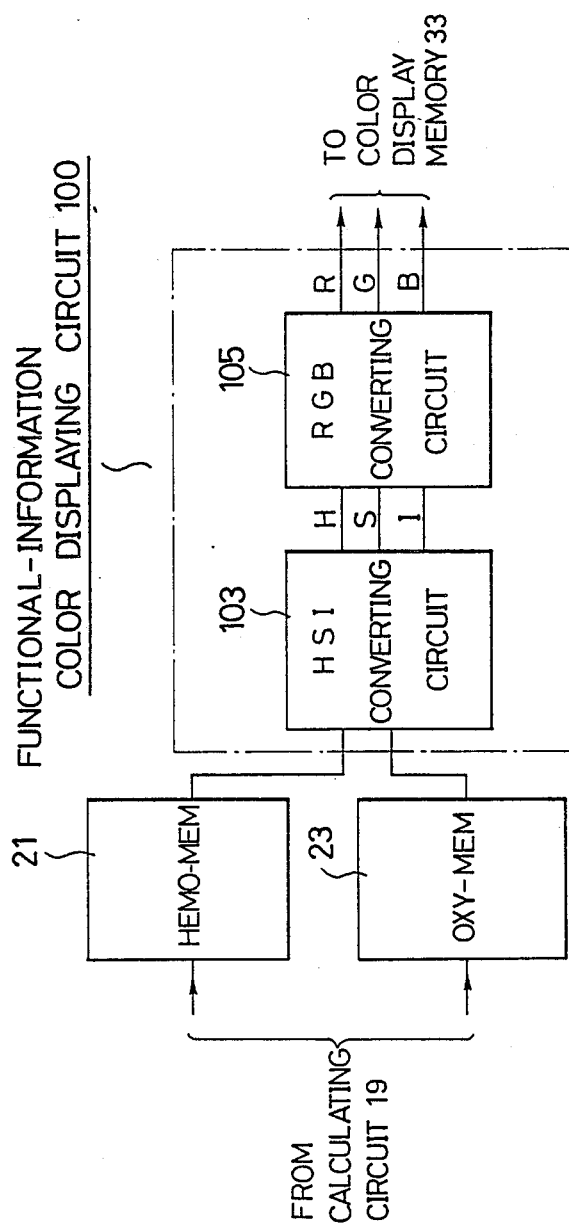
FIG. 6 is a block diagram of an internal circuit of the functional-information color displaying circuit 100 employed in the endoscope apparatus shown in FIG. 5.

An internal circuit of this functional-information color displaying circuit 100. As obvious from FIG. 6, the color displaying circuit 100 is arranged by an HSI converting circuit 103 and a RGB converting circuit 105.

As previously described, the functional information data, i.e., the concentration of hemoglobin under the mucous membrane and the oxygen saturation of hemoglobin which have been calculated in the calculating circuit 19, are stored in the hemoglobin-concentration image memory 21 and hemoglobin-oxygen saturation image memory 23. Similarly, the memory capacities of these image memory devices 21 and 23 are selected to be 512 bytes.

The functional-information data read out from the memory devices 21 and 23 are supplied to the color displaying circuit 100.

In the HSI circuit 103 of the functional-information color displaying circuit 100, a determination is made to the color values in accordance with the functional information data, and thereafter the color values are converted in the RGB converting circuit 105 into the R signal, G signal, and B signal, respectively.

FUNCTIONAL-INFORMATION COLOR DISPLAYING CIRCUIT

The selection of the color values in the HSI converting circuit 103 is performed as follows.

A hue (H) is allocated to the concentration of hemoglobin, saturation (S) is allocated to the oxygen saturation, and intensity (I) corresponds to a constant.

In the second preferred embodiment, the hue is changed from blue (cold color) to red (warm color), which is directly proportional to an increase in the concentration of hemoglobin. Then, the color-converted functional information data are supplied to the RGB converting circuit 105, whereby predetermined R.G.B data are obtained therefrom.

The data relating to the colors which have been determined every pixel are sent to the display memory 27 and stored therein. The memory capacity of the display memory 27 is selected to be 1.5 K bytes, similarly, which corresponds to the data acquired during 1 horizontal scanning period of the color image to be displayed on the display unit 30.

The color information data read out from the display memory 27 are converted in the D/A converter 29 into the corresponding analog color information signal, and thereafter displayed as the color image on the display unit 30.

As previously described, the colors of the respective pixels of the above-described color image correspond to the combination of two functions of functional information every pixel, and therefore the above-described color image represents the above-described two functions of the functional information.

The operations of the second preferred embodiment are summarized as follows. The functional information data read out from the corresponding functional-information data memories 21 and 23 are furnished to either the HSI converting circuit 103 or an HSV converting circuit (will be discussed later), where the hue, saturation and intensity are allocated to the functional information data. Thereafter, the resultant functional information data are converted in the RGB converting circuit into the R.G.B signals. Accordingly, these R.G.B signals are displayed on the display unit 30 as the color image.

ADVANTAGES OF SECOND EMBODIMENT OF THE ENDOSCOPE

While it has been described in detail, the electronic endoscope apparatus according to the second preferred embodiment of the invention provides the following advantages.

Various functional information is allocated to the typical three attributes of the color primary elements, i.e., a hue (H), saturation (S) and luminosity (I or V). This implies that the functional information relating to the biological body under examination can be displayed as the color image based upon this logical theory. Therefore, such a functional-information color image can easily be observed by an operator, as compared with the conventional B/W image. Moreover, in the conventional electronic endoscope apparatus, the so-called "quasi-color display" where the combinations of the R.G.B data are arbitrarily allocated to the various functions of the functional information without any definite allocation basis. However, according to the second preferred embodiment, the various functions of the functional information can be logically grasped from the functional-information colored image.

MODIFICATIONS

The present invention is not, obviously, limited to the above-described preferred embodiments, but may be modified.

First, as the modified brightness converter 5, the R', G', and B' data supplied from the A/D converter 13 may be directly added with each other, and scaling-processed so as to be converted into 8-bit Y data. The 8-bit Y data corresponds to the brightness of the light incident upon the CCD image sensor.

Figure 7:
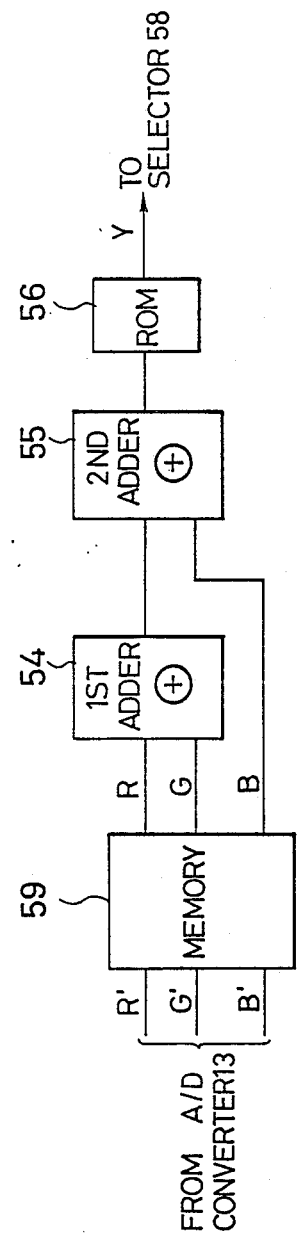
FIG. 7 is a schematic block diagram of another brightness converting circuit according to the invention.

Also, as illustrated in FIG. 7, instead of the first to third ROMs 51 to 53 employed in the brightness converter 5 shown in FIG. 4, a memory 59 is alternatively connected to the input terminals of the first adder 54. In this memory 59, the R', G', B' data are temporarily stored. The subsequent signal processing method is the same as that of the brightness converter 5. Therefore no further explanation is made.

In FIG. 8, there is shown another light source 7 of FIG. 3.

Figure 8B:
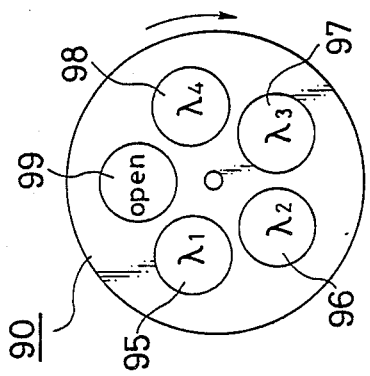
FIG. 8B shows the light source used with a filter disc.
Figure 8A:
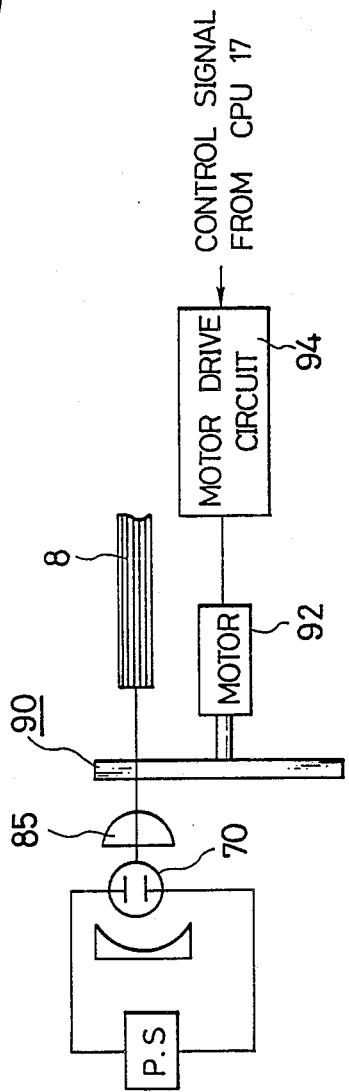
FIG. 8A schematically illustrates another light source according to the invention.

In FIG. 8A, only a xenon lamp 70 is employed which also functions as the above-described dye lasers 71 to 74. That is, a filter disk 90 illustrated in FIG. 8B, is interposed between the xenon lamp 70 and the light inlet of the scope 8. This filter disk 90 is coupled to a motor 92 which is driven under the control of a motor drive circuit 94. In response to a control signal derived from CPU 17, the motor drive circuit 94 controls the rotations of the filter disk 90. Four different filters 95 to 98 are mounted on the filter disk 90 in a predetermined order as shown in FIG. 8B. With this arrangement, the xenon light emitted from the xenon lamp 70 penetrates through one of these filters 95 to 98 so that the xenon light incident upon the selected filter is converted into the light having the desired wavelength ($\lambda_1$ to $\lambda_4$). The converted light is then incident upon the light inlet of the filter 8. Also, a through hole 99 is formed on this filter disk 90 so that the xenon light is directly traveled to the light inlet of the fiber scope 8 for the normal endoscope photographying operation.

According to the present invention, the numbers of the image memory units to be employed and of the monochromatic light may be varied in accordance with the number of the functions of the functional information. For instance, when only a concentration of hemoglobin of blood under mucous membrane is displayed as the functional information, two image memory units are sufficient. The monochromatic light having the wavelengths of 569 nm and 650 nm may be utilized only.

In the data transfer of the above-described electronic endoscope apparatuses, from the four image memory units 1 to 4 to the display unit 30, the data acquired during the 1 horizontal scanning period of the B/W image are transferred as one data transfer unit. The complete one image data, or one pixel data may be alternatively transferred.

In the second preferred embodiment, two different functions of the functional information, i.e., the concentration of hemoglobin under the mucous membrane and the oxygen saturation of hemoglobin, were displayed. Alternatively, only one functional information may be displayed. That is, to display the concentration of hemoglobin, the concentration of hemoglobin is allocated in the HSI converting circuit 103 to the hue (H), and both the saturation (S) and intensity (I) are constant. To the contrary, the hemoglobin oxygen saturation is allocated to the hue (H), and both the saturation (S) and intensity (I) are constant in order to display the hemoglobin oxygen saturation.

It is apparent that allocation of the H, S, and I is not limited to the above condition. The saturation (S) may be allocated to the concentration of hemoglobin, whereas the hue (H) may be allocated to the hemoglobin oxygen saturation, which gives the same effect to those of the second preferred embodiment.

Furthermore, the hue (H) may be allocated to, for instance, the concentration of hemoglobin, whereas the saturation (S) may be allocated to the fluctuation in the concentration of hemoglobin adjacent to the respective pixels, and the intensity (I) may be selected to be constant.

In addition, an HSV converting circuit may be employed instead of the HSI converting circuit, which may achieve the same effects as those in the second preferred embodiment. In this modified example, the above-described intensity "I" should be substituted by value "V".

As previously described, the idea of the present invention may be applied to another type of an electronic endoscope apparatus where an imaging sensor such as a vidicon is mounted on the fiber scope operation unit. The same advantages of the first and second preferred embodiments may be achieved in this case.

What is claimed is:

1. An electronic endoscope apparatus comprising:
   light source means for separately producing colored light having a predetermined light-wave band and monochromatic light having a plurality of different wavelengths;
   scope means for producing an image single of a biological body under examination while the biological body is irradiated by one of said colored light and monochromatic light;
   color signal processing means for processing said image signal derived from scope means so as to obtain a color television signal;
   means for converting the brightness of the color television signal acquired while said biological body is irradiated by one of said monochromatic light wave lengths to obtain a brightness-converted image signal;
   a plurality of memories, one associated with each wavelength of said monochromatic light and a color image memory for storing the calculated functional information; and,
   calculating means for calculating a plurality of brightness-converted image signals to obtain a functional-information signal representative of functional information on said biological body.

2. An electronic endoscope apparatus as claimed in claim 1, further comprising;
   first memory means including a plurality of image memory units for temporarily storing a plurality of brightness-converted image signals into the corresponding image memory units.

3. An electronic endoscope apparatus as claimed in claim 2, wherein said first memory means is constructed of first, second, third and fourth image memory units, said first image memory unit storing the brightness-converted image signal acquired while the biological body is irradiated by the monochromatic light having a wavelength of 569 nm (nanometers); said second image memory unit storing the brightness-converted image signal acquired while the biological body is irradiated by the monochromatic light having a wavelength of 577 nm; said third image memory unit storing the brightness-converted image signal acquired while the biological body is irradiated by the monochromatic light having a wavelength of 586 nm, and said fourth image memory unit storing the brightness-converted image signal acquired while the biological body is irradiated by the monochromatic light having a wavelength of 650 nm.

4. An electronic endoscope apparatus as claimed in claim 1, further comprising:
   second memory means for temporarily storing first data on a concentration of hemoglobin of said biological body obtained in the calculating means; and,
   third memory means for temporarily storing second data on an oxygen saturation of hemoglobin of said biological body obtained in the calculating means.

5. An electronic endoscope apparatus as claimed in claim 1, wherein said light source means includes:
   a xenon lamp for producing said color light having a predetermined light-wave band for photographing the biological body;
   a plurality of dye lasers for independently producing a plurality of monochromatic light having a plurality of different wavelengths, and
   light selecting means for selecting one of said color light from the xenon lamp and the plurality of monochromatic light from the dye lasers.

6. An electronic endoscope apparatus as claimed in claim 5, wherein said light selecting means includes:
   a mirror polygon for reflecting laser light of the chroma laser; and
   a mirror drive circuit for rotationally controlling the mirror polygon so as to select the plurality of monochromatic light.

7. An electronic endoscope apparatus as claimed in claim 1, wherein said light source means includes:
   a xenon lamp for producing said color light having a predetermined light-wave band;
   a filter disk having a through hole through which said color light passes directly, and a plurality of filters through which said corresponding monochromatic light pass: and
   a filter disk driver for rotationally driving said filter disk so as to select one of said color light passed through the through hole and the plurality of monochromatic light passed through the filters.

8. An electronic endoscope apparatus as claimed in claim 1, wherein said brightness converting means includes:
   ROM (read only memory) means for converting nonlinearity of said brightness-converted image signals derived from the brightness converting means to obtain a plurality of linear brightness-converted image signals (R:G:B), adder means for adding said plurality of linear brightness-converted image signals (R:G:B) to obtain an added brightness-converted image signal; and, a selector for selecting a desired brightness-converted image signal from the added brightness-converted image signal.

9. An electronic endoscope apparatus as claimed in claim 8, wherein said ROM means is constructed of four read only memory units.

10. An electronic endoscope apparatus as claimed in claim 8, wherein said adder means includes first adder for adding first and second linear brightness-converted image signals to obtain a first added linear brightness-converted image signal: and, a second adder for adding said added linear brightness-converted image signal with a four linear brightness-converted image signal.

11. An electronic endoscope apparatus as claimed in claim 8 further comprising:

a scaling ROM for scaling said added brightness-converted image signals.

12. An electronic endoscope apparatus comprising:

light source means for separately producing colored light having a predetermined light-wave band and a plurality of monochromatic lights having different wavelengths;

scope means for producing an image signal of a biological body under examination while the biological body is irradiated by one of said colored lights and monochromatic light of one wavelength;

color signal processing means for processing said image signal derived from scope means so as to obtain a color television signal;

means for converting the brightness of the color television signal acquired while said biological body is irradiated by one of said monochromatic lights to obtain a brightness-converted image signal;

calculating means for calculating a plurality of brightness-converted image signals to obtain a functional-information signal representative of functional information on said biological body; the information provided by the functional image being allocated to one of hue, luminance or color saturation; and, color displaying means for allocating color displaying elements to the functional information of said functional-information signal.

13. An electronic endoscope apparatus as claimed in claim 12, wherein said color displaying means includes:

a first converting circuit for converting said functional-information signal into a plurality of color-changed signals; and a second converting circuit for converting said color-changed signals into three colored signals.

14. An electronic endoscope apparatus as claimed in claim 13, wherein said first converting circuit converts said functional-information signal based upon hue, saturation and luminosity.

15. An electronic endoscope apparatus as claimed in claim 12, further comprising:

first memory means including a plurality of image memory units for temporarily storing a plurality of brightness-converted image signals into the corresponding image memory units.

16. An electronic endoscope apparatus as claimed in claim 15, wherein said first memory means is constructed of first, second, third and fourth image memory units, said first image memory unit storing the brightness-converted image signal acquired while the biological body is irradiated by the monochromatic light having a wavelength of 569 nm (nanometers); said second image memory unit storing the brightness-converted image signal acquired while the biological body is irradiated by the monochromatic light having a wavelength of 577 nm; said third image memory unit storing the brightness-converted image signal acquired while the biological body is irradiated by the monochromatic light having a wavelength of 586 nm, and said fourth image memory unit storing the brightness-converted image signal acquired while the biological body is irradiated by the monochromatic light having a wavelength of 650 nm.

17. An electronic endoscope apparatus as claimed in claim 12, further comprising:

second memory means for temporarily storing first data on a concentration of hemoglobin of said biological body obtained in the calculating means; and, third memory means for temporarily storing second data on an oxygen saturation of hemoglobin of said biological body obtained in the calculating means (19).

18. An electronic endoscope apparatus as claimed in claim 12, wherein said light source means includes:

a xenon lamp for producing said color light having a predetermined light-wave band for photographying the biological body;

a plurality of dye lasers for independently producing a plurality of monochromatic light having a plurality of different wavelengths, and light selecting means for selecting one of said color light from the xenon lamp and the plurality of monochromatic light from the dye lasers.

19. An electronic endoscope apparatus as claimed in claim 18, wherein said light selecting means includes:

a mirror polygon for reflecting laser light of the dye laser; and a mirror drive circuit for rotationally controlling the mirror polygon so as to select the plurality of monochromatic light.

20. An electronic endoscope apparatus as claimed in claim 12, wherein said light source means includes:

a xenon lamp for producing said color light having a predetermined light-wave band;

a filter, disk having a through hole through which said color light passes directly, and a plurality of filters through which said corresponding monochromatic light pass; and a filter disk driver for rotationally driving said filter disk so as to select one of said color light passed through the through hole and the plurality of monochromatic light passed through the filters.

21. An electronic endoscope apparatus as claimed in claim 12, wherein said brightness converting means includes:

ROM (read only memory) means for converting non-linearity of said brightness-converted image signals derived from the brightness converting means to obtain a plurality of linear brightness-converted image signals, adder means for adding said plurality of linear brightness-converted image signals to obtain an added brightness-converted image signal; and, a selector for selecting a desired brightness-converted image signal from the added brightness-converted image signal.

22. An electronic endoscope apparatus as claimed in claim 21, wherein said ROM means is constructed of four read only memory units.

23. An electronic endoscope apparatus as claimed in claim 21, wherein said adder means includes first adder for adding first and second linear brightness-converted image signals to obtain a first added linear brightness-converted image signal; and, a second adder for adding said added linear brightness-converted image signal with a fourth linear brightness-converted image signal.

24. An electronic endoscope apparatus as claimed in claim 21 further comprising:
a scaling ROM for scaling said added brightness-converted image signals.

* * * * *